(12) United States Patent
Dobson

(10) Patent No.: US 11,331,430 B2
(45) Date of Patent: May 17, 2022

(54) INJECTION DEVICE

(71) Applicant: Owen Mumford Ltd, Oxfordshire (GB)

(72) Inventor: Matthew John Dobson, Oxfordshire (GB)

(73) Assignee: Owen Mumford Limited, Oxfordshire (GB)

(*) Notice: Subject to any disclaimer, the term of this patent is extended or adjusted under 35 U.S.C. 154(b) by 209 days.

(21) Appl. No.: 16/494,489

(22) PCT Filed: Mar. 15, 2018

(86) PCT No.: PCT/GB2018/050664
§ 371 (c)(1),
(2) Date: Sep. 16, 2019

(87) PCT Pub. No.: WO2018/167494
PCT Pub. Date: Sep. 20, 2018

(65) Prior Publication Data
US 2020/0086053 A1   Mar. 19, 2020

(30) Foreign Application Priority Data
Mar. 15, 2017   (GB) ..................................... 1704141

(51) Int. Cl.
*A61M 5/20* (2006.01)
*A61M 5/28* (2006.01)
(Continued)

(52) U.S. Cl.
CPC .......... *A61M 5/283* (2013.01); *A61M 5/2033* (2013.01); *A61M 5/3146* (2013.01);
(Continued)

(58) Field of Classification Search
CPC .......... A61M 5/2033; A61M 2005/206; A61M 2005/2073; A61M 2005/2013; A61M 2005/208
See application file for complete search history.

(56) References Cited

U.S. PATENT DOCUMENTS

| | | | | |
|---|---|---|---|---|
| 2013/0035645 A1* | 2/2013 | Bicknell | ............. | A61M 5/3202 604/198 |
| 2013/0289492 A1* | 10/2013 | Brereton | ............. | A61M 5/2033 604/198 |

(Continued)

FOREIGN PATENT DOCUMENTS

| | | | |
|---|---|---|---|
| EP | 2 468 334 A1 | 6/2012 | |
| EP | 2 489 380 A1 | 8/2012 | |

(Continued)

OTHER PUBLICATIONS

Great Britain Search Report dated Aug. 14, 2017, in corresponding application GB1704141.9.
(Continued)

*Primary Examiner* — Emily L Schmidt
(74) *Attorney, Agent, or Firm* — Quarles & Brady LLP

(57) ABSTRACT

Disclosed is an injection device for receiving a syringe therein and for delivering a dose of medicament from the syringe, the injection device including: an insertion driver configured to drive the syringe forwards within the injection device for inserting a needle of the syringe into an injection site; an interlock mechanism configured to retain the insertion driver in a primed state and, when actuated, to allow the insertion driver to drive the syringe forwards; and an interlock actuator moveable between a stowed position and an operable position and configured on movement from the stowed position to the operable position to couple to an actuation system such that movement from the operable (Continued)

position back towards the stowed position actuates the interlock mechanism.

20 Claims, 11 Drawing Sheets

(51) Int. Cl.
    *A61M 5/31*     (2006.01)
    *A61M 5/32*     (2006.01)
(52) U.S. Cl.
    CPC .......... *A61M 5/3204* (2013.01); *A61M 5/326* (2013.01); *A61M 2005/206* (2013.01); *A61M 2005/2073* (2013.01)

(56) References Cited

U.S. PATENT DOCUMENTS

2014/0276589 A1    9/2014    Markussen
2015/0367072 A1   12/2015   Constantineau et al.

FOREIGN PATENT DOCUMENTS

| WO | 2006/057604 A1 | 6/2006 |
| --- | --- | --- |
| WO | 2008/112472 A2 | 9/2008 |
| WO | 2012/049484 A2 | 4/2012 |
| WO | 2012/085580 A1 | 6/2012 |
| WO | 2013/016832 A1 | 2/2013 |
| WO | 2015/011488 A1 | 1/2015 |
| WO | 2015/169608 A1 | 11/2015 |
| WO | 2016/118688 A1 | 7/2016 |
| WO | 2016/174249 A1 | 11/2016 |
| WO | 2016/189286 A1 | 12/2016 |
| WO | 2017/007850 A1 | 1/2017 |

OTHER PUBLICATIONS

International Search Report dated Jul. 9, 2018, in corresponding application PCT/GB2018/050664.

* cited by examiner

INJECTION DEVICE

CROSS-REFERENCE TO RELATED APPLICATIONS

The present application represents the United States National Stage of International Application No. PCT/GB2018/050664, filed Mar. 15, 2018, which claims priority to British Patent Application Serial No. GB 1704141.9, filed Mar. 15, 2017, and entitled, "INJECTION DEVICE," the contents of which are incorporated herein by reference in their entirety.

TECHNICAL FIELD

This invention relates to injection devices for delivering a dose of medicament from a syringe. In particular, but not exclusively, the invention relates to an autoinjector type device which facilitates powered or power assisted needle insertion and injection.

BACKGROUND

Injection devices are used for the convenient administration of medicaments. For example, injection devices (which may typically be in the form of a pen injector) may be used for providing a single metered dose of a medicament, for example such as Epinephrine in an emergency or for providing regular metered doses of a medicament such as Insulin. Such devices may be either single use "disposable" devices in which the device is typically provided with a syringe already installed, and which is not user-replaceable, or "reusable" devices which allow the user to replace the syringe when the medicament has been used.

It is noted that whilst the term "syringe" is used herein for clarity and consistency, this term is not intended to be limiting. In some arrangements the syringe may for example be a cartridge (which, for example, may be arranged to receive a disposable needle) or other medicament container. In some arrangements the syringe/cartridge/medicament container may be formed integrally with the (or part of the) injection device.

Injection devices may be provided in the form of an "autoinjector" device, in which, in addition to automating the delivery of the medicament, the device is also arranged to automate the insertion of a needle into the skin prior to the delivery of the medicament.

Injection devices generally comprise a delivery arrangement which is arranged to automatically deliver a dose from the syringe, and optionally (in the case of an autoinjector) to first displace the syringe within the housing to cause needle penetration. The delivery arrangement generally acts via a plunger which includes or engages a piston (also referred to as a "bung") which is slidably provided within the syringe. In the case of an autoinjector the initial static friction or "stiction" between the bung and syringe resists forward movement of the piston relative to the syringe such that initially the delivery arrangement moves the syringe and piston forward into the needle insertion position. Here, further movement of the syringe is blocked and the delivery arrangement will continue to move forward, overcoming the stiction, and moving the piston and the bung through the syringe.

A common form of delivery arrangement includes a driver mechanism which biases the plunger forwardly and a trigger mechanism which holds the plunger (directly or indirectly) against the force of the driver mechanism until the trigger is released. For example the driver mechanism may comprise a drive spring (for example a compression spring) which is held in an energised (or primed position) prior to release by the trigger.

An injection device of the autoinjector type is described in WO2016/189286.

At least some embodiments of the invention seek to provide an improved injection device which may help to address some of these problems.

SUMMARY

According to an aspect of the invention, there is provided an injection device for receiving a syringe therein and for delivering a dose of medicament from the syringe, the injection device comprising: an insertion driver configured to drive the syringe forwards within the injection device for inserting a needle of the syringe into an injection site; an interlock mechanism configured to retain the insertion driver in a primed state and, when actuated, to allow the insertion driver to drive the syringe forwards; and an interlock actuator moveable between a stowed position and an operable position and configured on movement from the stowed position to the operable position to couple to an actuation system such that movement from the operable position back towards the stowed position actuates the interlock mechanism.

Optionally, the interlock actuator comprises a lock out shroud at least partially received within the injection device.

Optionally, the lock out shroud is configured to move forward from the stowed position such that it extends from a forward end of the injection device in the operable position.

Optionally, the interlock actuator further comprises one or more of at least part of a syringe carrier and at least part of a barrel of the syringe.

Optionally, wherein the interlock mechanism comprises a rearwardly extending interlock ramp and a lug linearly coupled to the syringe and forward biased onto the interlock ramp to resist travel of the lug rearwards on the interlock ramp.

Optionally, the lug is linearly coupled to the interlock actuator such that movement of the interlock actuator from the operable position towards the stowed position causes the lug to travel rearwards on the interlock ramp.

Optionally, the interlock mechanism further comprises a vertical slot extending from a rearward end of the interlock ramp, and wherein the interlock actuator is moveable from the stowed position towards the operable position to align the lug with the vertical slot.

Optionally, the insertion driver is configured to drive the lug forwards into the vertical slot and thereby to drive the syringe forwards to insert the needle into the injection site.

Optionally, the insertion driver is further configured to bias the interlock actuator from the stowed position towards the operable position, the injection device further comprising a stowage lock configured to retain the interlock actuator in the stowed position until release thereof.

Optionally, the stowage lock comprises a cap removably fitted to the injection device, and wherein removal of the cap releases the stowage lock.

Optionally, the injection device further comprises a forwardly extending extension ramp, the forward end of the extension ramp meeting the forward end of the interlock ramp to form a V-shape, wherein the lug is linearly coupled to the interlock actuator and wherein release of the stowage lock allows the insertion driver to cause the lug to travel down the extension ramp such that the lug is at the bottom of the V-shape and the interlock actuator is in the operable position.

Optionally, the actuation system comprises a guide system configured, on movement of the interlock actuator from the operable position towards the stowed position, to ensure the lug travels along the interlock ramp and not along the extension ramp.

Optionally, the guide system comprises a track operable with the lug to guide the lug to ensure it travels along the interlock ramp and not along the extension ramp.

Optionally, a biasing means resists actuation of the interlock mechanism, and wherein the actuation system is configured to provide geared movement of the interlock actuator and the interlock mechanism against the biasing means.

Optionally, the injection device further comprises an actuation track and a pip configured to move within the actuation track, wherein the pip is rotationally coupled to the lug such that it moves within an interlock section of the actuation track when the lug moves on the interlock ramp, and wherein the interlock section of the actuation track has a steeper rearward incline than the interlock ramp.

Optionally, the guide system comprises the pip and the actuation track, and wherein the pip and the actuation track are configured to cooperate to guide the pip into the interlock section.

Optionally, the pip has a tear drop shape with the tip facing substantially rearward.

Optionally, the pip is skewed such that the tip is biased in one direction away from a longitudinal axis of the for guiding the pip into the interlock section.

Optionally, a length of the injection device is less when the interlock actuator is in the stowed position than when the interlock actuator is in the operable position.

According to an aspect of the invention, there is provided a rear section of an injection device for attachment to a front section to form the injection device, wherein the injection device is for receiving a syringe therein and for delivering a dose of medicament from the syringe, the rear section comprising: an insertion driver configured to drive the syringe forwards within the injection device for inserting a needle of the syringe into an injection site; an interlock mechanism configured to retain the insertion driver in a primed state and, when actuated, to allow the insertion driver to drive the syringe forwards; and an actuation system configured to couple to an interlock actuator when the interlock actuator is moved from a stowed position to an operable position such that movement of the interlock actuator from the operable position back towards the stowed position actuates the interlock mechanism.

DETAILED DESCRIPTION

In the following embodiments, the terms "forward" and "front" refer to the patient facing end of the injection device or component thereof. In other words, the front end of the injection device is the end proximal to the injection site during use. Likewise, the term "rear" refers to the non-patient end of the injection device assembly or component thereof. In other words, the term "rear" means distant or remote from the injection site during use. Further, the terms up, down and vertical refer to the situation in which an injection device is held so that the forward end is lowermost and the injection device itself is held vertically. Axial, radial and circumferential are used herein to conveniently refer to the general directions relative to the longitudinal direction of the injection device (or components thereof).

The skilled person will, however, appreciate that these terms are not intended to be narrowly interpreted (and for example, the injection device may have a non-circular and/or irregular form). Typically, regardless of the chosen injection device external profile the syringe or cartridge will have a conventional, generally cylindrical, elongate form and will include or be associated with a needle extending longitudinally from a forward end thereof. Thus, the longitudinal axis of the injection device will typically substantially coincide with (or be parallel to) the axial direction of the syringe or cartridge.

Figure 1:
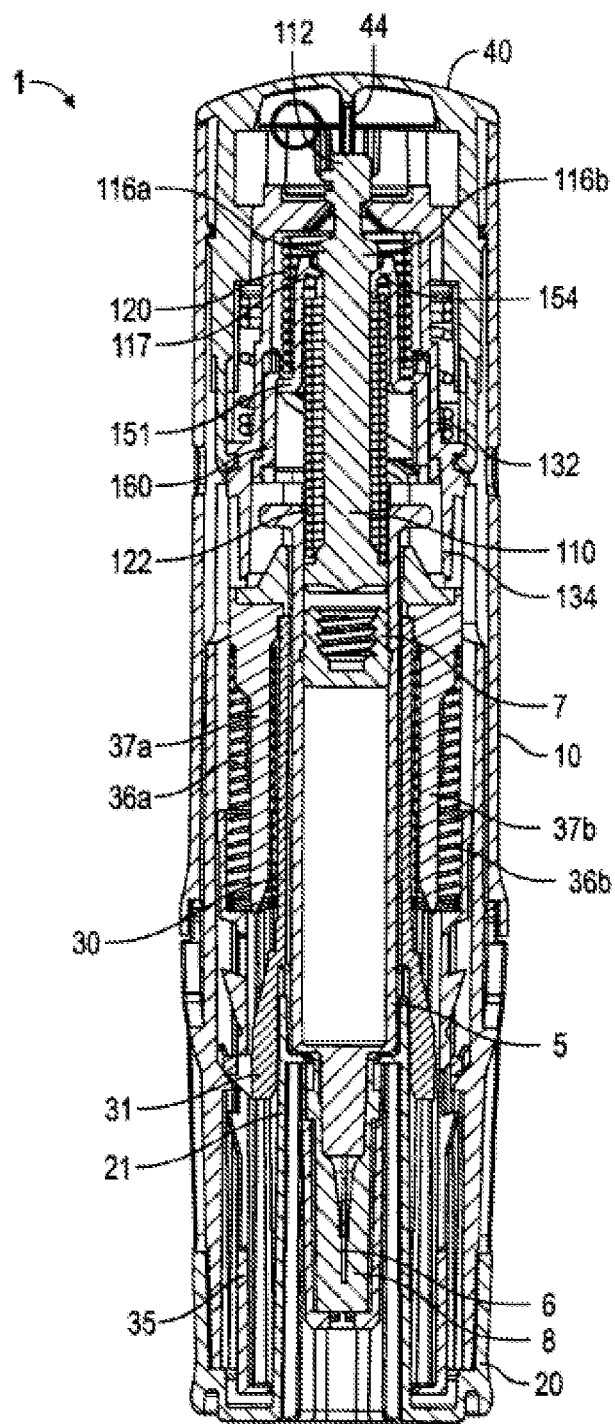
FIG. 1 is a cross-sectional view of an injection device.

FIG. 1 shows a cross-sectional view of a prior art autoinjector 1 as disclosed in WO2016/189286. The autoinjector comprises a housing 10 within which is provided a syringe 5 of medicament. The housing 10 has a generally elongate tubular shape with a generally oval cross-sectional profile (and has a longitudinal axis running through the centre of the syringe).

The syringe 5 is a conventional syringe having a bung 7 within its body and a needle 6 at its forward end which may be initially protected (so as to remain sterile) by a removable needle shield or "boot" 8. The illustrated autoinjector 1 is generally intended to be a single use device (although the skilled person will appreciate that the invention is not limited to such devices) and, therefore, the view of FIG. 1 may typically represent a fully assembled, ready to use device as provided to an end user. A cap 20 is provided which closes the forward end of the autoinjector 1 prior to use. The cap 20 may include an internal formation, comprising rearward extending members 21, arranged to engage the removable needle shield 8 of the syringe 5 such that removal of the cap 20 from the housing 10 during use also removes the removable needle shield 8 from the syringe 5.

The autoinjector 1 may conveniently be considered to comprise a forward subassembly in a forward portion of the housing 10 and a rearward assembly in a rearward portion of the housing 10. The two housing portions may be snap fit together during assembly. The forward subassembly may comprise the components which surround and/or are initially forward of the syringe 5. The rearward subassembly may comprise those components which are initially rearward of the syringe 5.

A forward portion of the housing 10 may contain a syringe carrier 30 for movably mounting the syringe within the housing 10 to enable automatic needle penetration. It may be noted that prior to the removal of the cap 20, the rearward extending members 21 of the cap 20 underlie spring fingers 31 of the syringe carrier 30. This arrangement thus prevents inward movement of the spring fingers 31 prior to removal of the cap 20 and, therefore, blocks unlatching of the syringe carrier 30 and prevents movement relative to the housing 20.

A needle shroud (or lock out shroud) 35 is also provided and arranged to shroud the needle after use (when the syringe 5 and syringe carrier 30 are in a forward position) to prevent needle stick injuries. The shroud 35 may be activated by a pair of side-by-side shroud springs 36a, 36b carried on respective spring guides 37a, 37b. Operation of the shroud 30 and carrier 35 is not described here in any detail. However, it may be noted that the arrangement substantially corresponds to the arrangement described in WO2012/085580.

A rearward portion of the housing 10 includes a trigger button 40 which is inserted into the rearward portion of the housing 10 from the rearward end so as to substantially close the rearward end of the housing 10. The trigger button 40 has a cup-like profile with side walls which are arranged to fit within (and be substantially concentric with) the rearward housing 30 and an end wall which closes the rear end of the housing. The trigger button 40 includes a pair of forwardly extending resilient arms 41a and 41b which are arranged to provide an engagement between the trigger button 40 and the injector 1.

Figure 2:
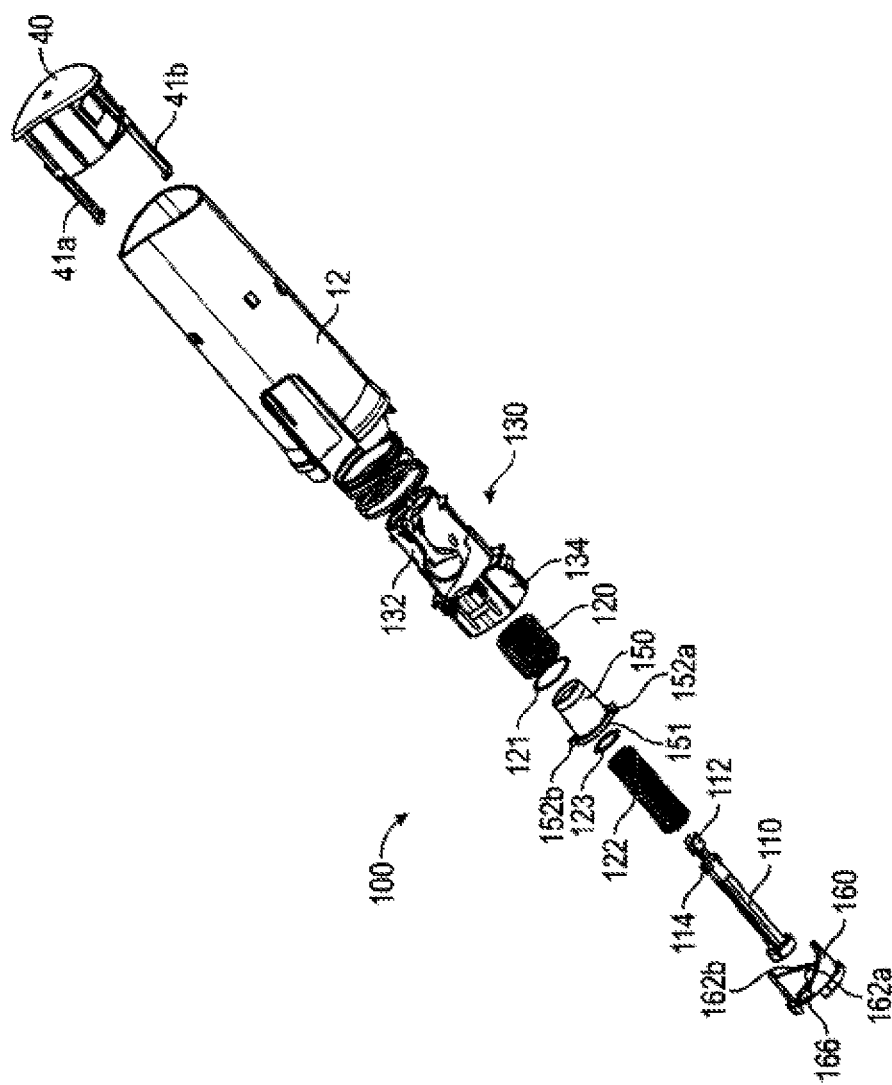
FIG. 2 is an exploded view of a rear section of an injection device.

The rearward portion of the housing 10 also includes a drive mechanism 100, best seen in FIG. 2. The drive mechanism 100 includes a plunger 110 which is arranged to engage the bung 7 of the syringe 5 in use. The plunger 110 is driven forwards in use by a pair of concentric drive springs 120 and 122 (although it will be appreciated that in other embodiments a single spring may be used). An intermediate drive member in the form of a collar 150 (which also functions as part of the velocity regulator as described below) is provided between the first 120 and second 122 drive springs. A pair of thrust washers 121, 123 are provided respectively between the first 120 and second 122 springs and the drive member/collar 150. A latch 130 is arranged concentrically around the drive springs 120, 122, intermediate member/collar 150 and plunger 110. The latch 130 is arranged to hold the plunger 110 against the bias of the springs 120, 122 until the latch is released via the trigger button 40. The latch 130 comprises a rear body portion 132 having a split cylinder profile and defining a latch aperture at its rear end and a forward connecting body portion 134. The basic functional operation of the drive mechanism 100 is substantially as described, for example, in the applicants' earlier International Patent Applications WO2012/049484 and WO2015/011488.

Figure 3:
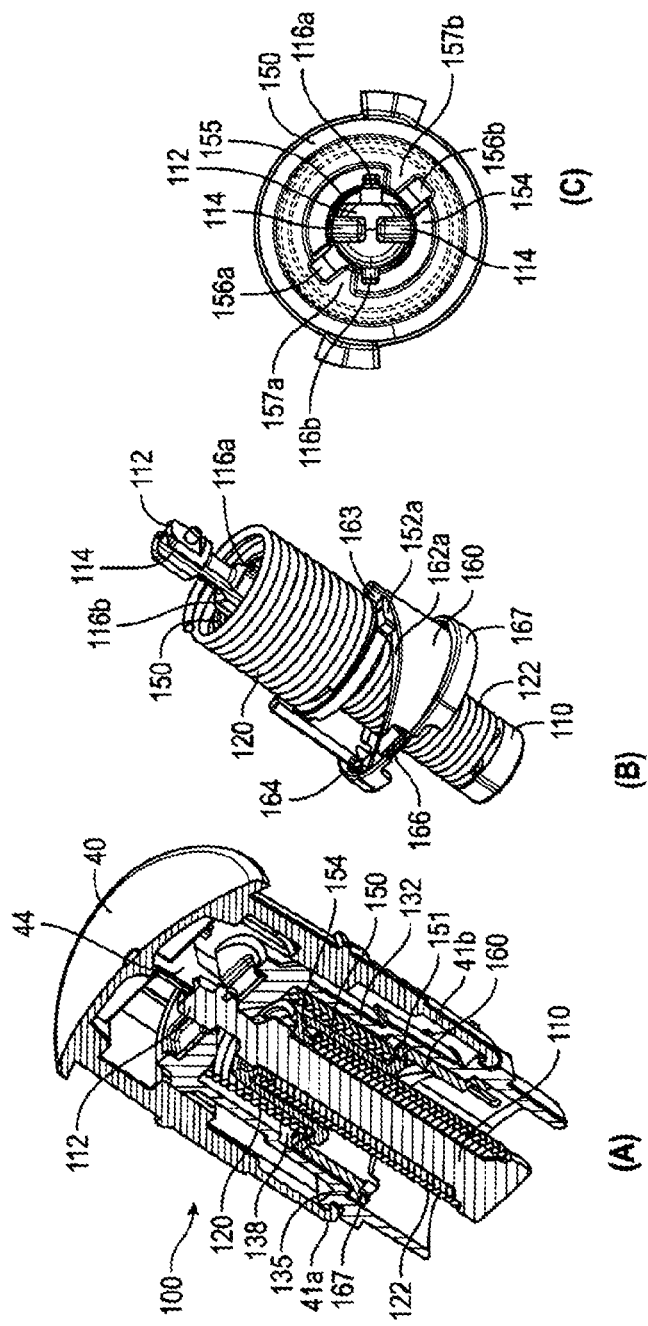
FIG. 3 is a cross-section view and partial end view of an actuation mechanism including a velocity regulator, in a pre-fired state.
Figure 4:
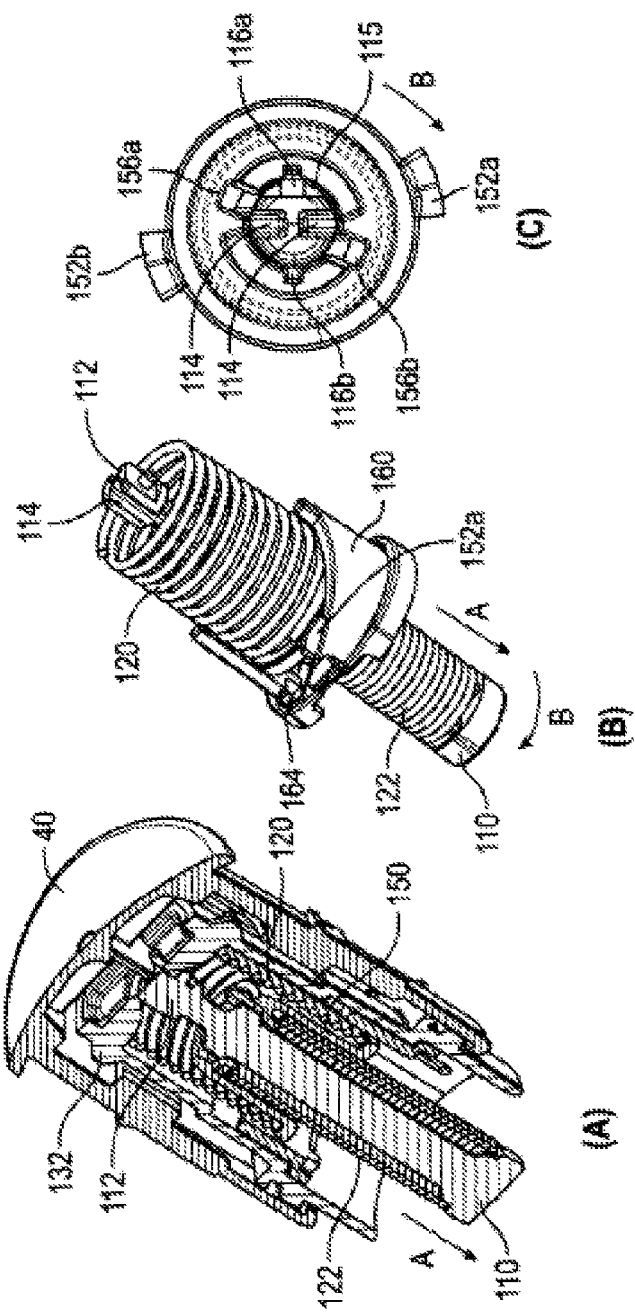
FIGS. 4 to 6 are sequential views corresponding to FIG. 3 during the activation of an autoinjection device.

The driver mechanism will now be described in further detail with particular reference to FIGS. 2 and 3. FIG. 2 shows an exploded view of a rearward subassembly of the autoinjector device 1 (in which it may be noted that the housing 10 includes a discreet rearward housing component 12). In FIG. 3a the housing is omitted for clarity and in FIGS. 3b and 3c only the components directly associated with the velocity regulator are shown for further clarity. As noted above, the driver mechanism includes a latch member 130 which is removably fixed into the housing 10 (by a snap fit arrangement) and initially retains the plunger 110 against the forward biasing force of the actuation springs 120 and 122 (which act via the intermediate member 150). At the rear of the injection device 1 is provided a trigger button 40 which may initially be retained in position by the pair of arms 41a, 41b. In a central portion of the inner surface of the rearward face of the button 40 a forwardly extending boss 44 is provided which may act to urge the plunger 110 out of engagement with the latch member 130 during activation (in a manner such as that described in the applicants earlier patent applications referred to above).

The boss 44 comprises an arrangement which is in splined engagement with the rearward head 112 of the plunger 110. It will be seen that the rearward end of the plunger 110 is provided with a pair of axially extending radial slots which extend forwardly from the head 112 and the boss 44 comprising a corresponding pair of projections. As will be explained in further detail below, this arrangement ensures that the plunger 110 is rotationally fixed relative to the trigger button 40. In turn the trigger button 40 is non-rotationally engaged with the housing 10 (for example, due to the non-circular shape of the housing 10 and trigger button 40 and/or the engagement between the legs 41a, 41b of the trigger button 40 and the latch 130).

The driver mechanism 100 of the autoinjector device 1 also includes a velocity regulator arranged to control or limit the initial velocity of the plunger 110 upon release of the driver mechanism. The velocity regulator utilises a cam member 152 which travels along a cam surface 162 which provides an inclined plane along which the cam member 152 will travel during actuation.

The cam surface 162 is conveniently provided on a cam body 160 which is engaged with the forward portion 134 of the latch 130 by a snap-fit arrangement including, for example, at least one latch member 166. To ensure proper alignment between the cam body 160 and the latch member 130 an alignment flange 167 may also be provided on the cam body 160 to abut a corresponding shoulder 135 in the latch 130. The cam body 160 may comprise a generally annular body with an external profile which matches the required internal profile of the latch 130. A pair of helical cam surfaces 162a, 162b are defined at the rearward end of the cam body and are forwardly sloped to define a pair of parallel cam paths which extend circumferentially around the interior of the injection device 1 whilst also being inclined forwardly in the manner of a partial screw thread. A correspondingly profiled shoulder may be provided rearward of the cam surface 162 on the interior surface of the latch 130 such that when the cam body is assembled with the latch 130 a slot or track 138 as defined (and configured to receive the cam members 152). Each cam surface 162 is provided with stop 163 at its rearward end (which acts to separate the separate cam paths defined by the cam body 160) and ends with a cut-out or aperture 164 at the forward most end of the cam surface 162.

The collar 150 acts as an intermediate drive member between the first compression spring 120 and second compression spring 122. Accordingly, the collar 150 includes an external radial flange 151 at its forward end which provides a seat for the first compression spring 120 and an internal radial flange 154 at its rearward end which provides a seat for the second compression spring 122. The thrust washers 121, 123 are disposed on the seats between the radial flanges 151, 154 of the collar and the springs 120, 122. The collar 150 is a generally cylindrical body and is provided with a pair of radially opposed outwardly extending lugs 152a, 152b. The lugs 152a, 152b are provided on a radially outer surface of the outwardly extending flange 151 (such that they do not impede either of the compression springs 120, 122). The internal flange 154 at the rear of the collar 150 includes an aperture 155 through which the head 112 of the plunger extends when the driver mechanism 100 is in the pre-fired (or primed) condition as shown in FIG. 3.

The aperture 155 is provided with a keyed profile defined by a cylindrical central aperture portion 155a and a pair of opposed radial slots 156. The cylindrical side walls of the collar 150 extend rearward slightly beyond the flange 154 so as to define a cylindrical cup which surrounds the flange 154 and the aperture 155. Inwardly radially extending stop members 157a, 157b may be provided adjacent to one side of the radial slots 156a and 156b.

A rearward portion of the plunger 110 which is axially rearward of the aperture 155 in the pre-fired configuration is provided with a profiled cross-section for engagement with the keyway defined by the aperture 155. This profiled portion is immediately forward of the head 112 of the plunger which is configured to be engaged by the latch 130. The profiled portion is defined by a pair of radially outwardly 20 extending projections 116a, 116b which provide a forward facing shoulder 117 is initially engaged with the rearward face of the flange 154. The radial projections 116a, 116b are configured such that they may pass through the radial slots 156a, 156b when the slots 156 and projections 116 are aligned.

The actuation sequence of the mechanism 100 and velocity regulator will now be described with reference to FIGS. 3 to 6. The pre-firing configuration of the driver mechanism 100 is shown in FIG. 3. In this configuration the head 112 of the plunger 110 is retained in the aperture of the latch 130. As such both the first compression spring 120 and the second compression spring 122 are in a compressed, energised, state. The trigger button 40 is in splined engagement with the rearward end of the plunger 110 via the boss 44 being positioned within the slots 114 at the rear of the plunger 110. The rearward portion 132 of the latch 130 is unable to expand to release the head 112 of the plunger 110 as part of the trigger button abuts an outer surface of the rearward section of the latch 132.

In this position the radial projections 116 of the plunger 110 are rearwardly positioned relative to the aperture 155 of the collar 150 and the relative rotational position of the plunger 110 and the collar 150 has been set during assembly such that the projections 116 are misaligned with the slots 156 and, in fact, it will be noted that the projections 116 may be abutting against the stops 157 of the collar 150. In this initial position the cam members 152 are positioned at a rearward end of the cam surfaces 162 and essentially abut against the stops 163 at the rearward most end of the cam surfaces 162.

In order to activate the device the user urges the trigger button 40 forward relative to the housing 10 of the autoinjector device 1 (having firstly carried out any required initiation steps such as removal of the cap from the forward end of the autoinjector device 1 and/or releasing any safety mechanisms, such as an interlock). The forward movement of the trigger button 40 moves the blocking arrangement of the cap 40 out of alignment with the rearward section 132 of the latch 130 and may also directly transmit a forward force onto the rear of the plunger 110 via the engagement of the boss 44 with the head 112 of the plunger 110. As the result of this trigger action, the head 112 of the plunger 110 is released from the trigger 130 freeing the rearward spring 120 to urge the plunger forwardly, in the direction of arrow A, via the outer flange 151 or the collar 150.

This forward movement causes the cam members 152a, 152b to travel along the inclined path of the cam surface 162a, 162b. As the first spring 120 expands its axial force is transmitted by the collar 150 through the fully compressed second compression spring 122 to the forward end of the plunger 110. However, initially the plunger 110 is unable to travel beyond the collar 150 as the radial projections 116 engage the internal flange 154 at the rear of the collar 150.

Due to the splined engagement between the trigger button 40 and the plunger 110 the collar 150 must rotate relative to the plunger 110, in the direction of the arrow B, as the cam members 152a, 152b travel along the cam surfaces 162a, 162b. The thrust washers 121, 122 prevent or reduce any frictional resistance to the rotation of the collar 150 by the springs 121, 122. As best seen in the end view of FIG. 4c, the resulting relative rotation of the collar 150 causes the aperture 155 to rotate relative to the radial projections 116a, 116b moving the projections off the stop surface 157 and towards the radial slots 156a, 156b.

Figure 5:
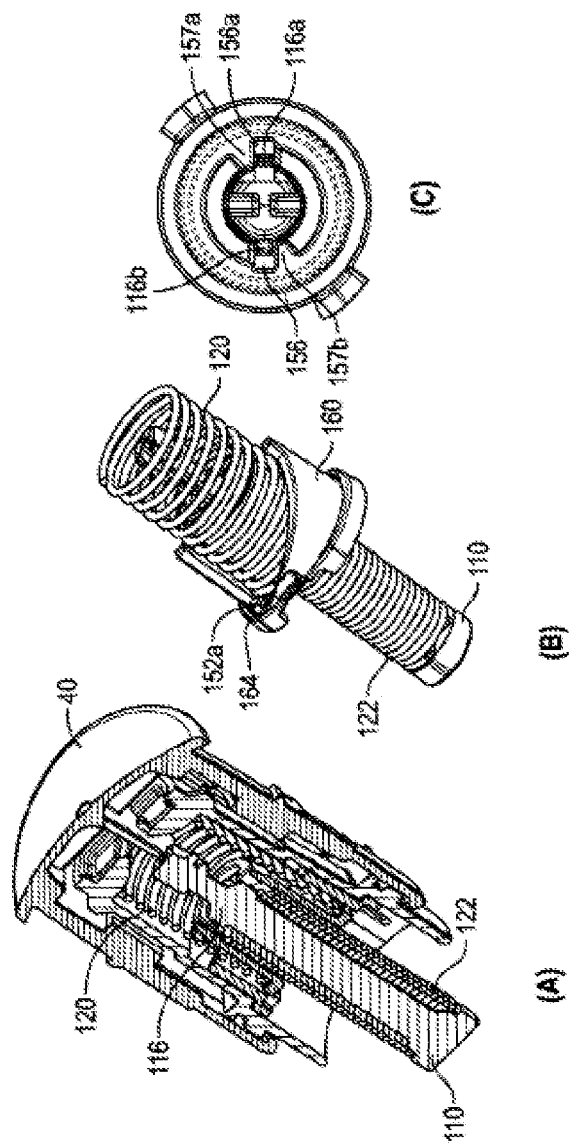

As the plunger 110 and collar 150 continue to move forwardly, the collar 150 reaches its fully rotated position as shown in FIG. 5. In the illustrated example the fully rotated position corresponds to approximately one half turn of the collar 150 (although the skilled person will appreciate that the particular configuration may vary depending on the profile of the cam surface and the required sequencing of the actuation mechanism 100). In this position the radial slots 156a, 156b have rotated into alignment with the radial projections 116a, 116b and the cam members 152a, 152b have also reached the end of the cam surface 162a, 162b and have moved into alignment with the cut-out/aperture 164 at the end of the cam path.

Figure 6:
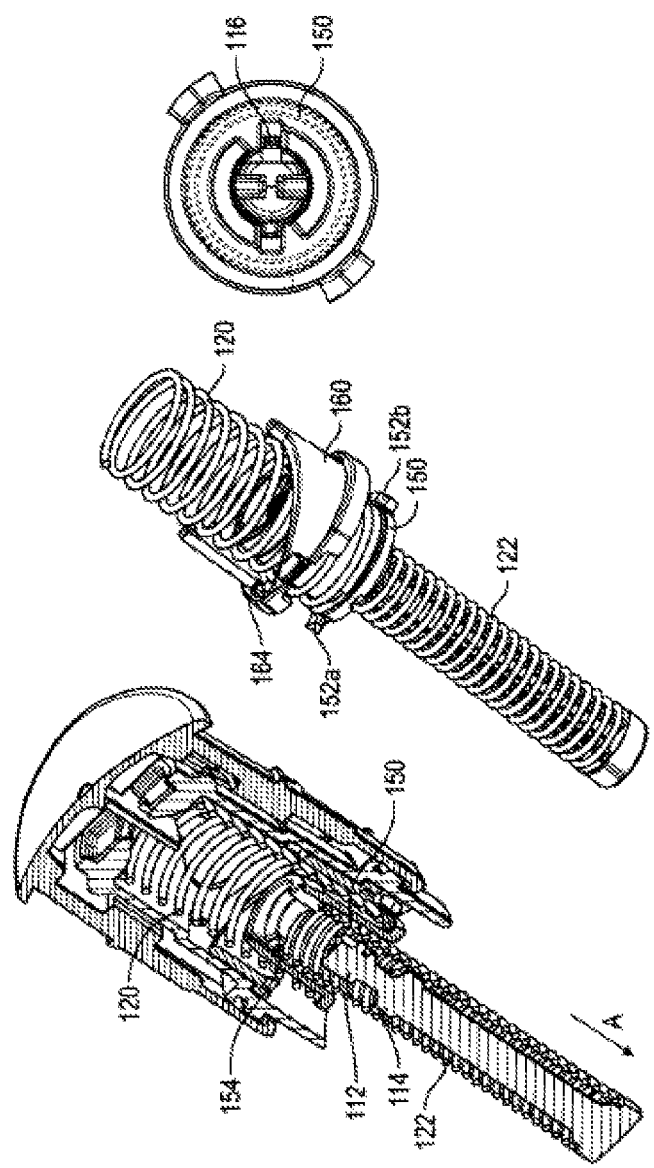

Accordingly, as shown in FIG. 6, the velocity regulator may now disengage so as to allow the plunger to continue freely forward (continuing in the direction of arrow A). In this forward movement the plunger 110 moves forward relative to the collar 150 due to the radial projections 116a, 116b passing through the radial slots 156a, 156b and the collar 150 is also allowed to pass forwardly of the cam body 160 due to the cam members 152a, 152b passing through the cut-outs 164. In other words, both the collar 150 and plunger 110 are disengaged and the collar 150 and cam body 160 are disengaged. In the illustrated embodiment the disengagements both occur substantially simultaneously (although the skilled person will appreciate that this may depend on the particular sequencing required). Once the velocity regulator is disengaged the forward motion of the plunger 110 is no longer regulated (but the skilled person will appreciate that the plunger may now be pressing against the medicament within the syringe 5 such that its motion is naturally damped).

Although the device has been described above with reference to one embodiment, it will be appreciated that various changes or modifications may be made. For example, the skilled person will appreciate that the timing of the disengagement between the components of the velocity regulator may depend on the particular configuration of the device. For example, the velocity regulator may be intended to slow/control the movement of the plunger 110 only during an initial movement in which the plunger 110 is brought into contact with the bung 7 of the syringe 5 (since manufacturing tolerances will usually make it necessary for the forward end of the plunger 110 to be initially spaced from the rearward end of the bung 7) so as to reduce impact thereto. Alternatively, or additionally, the velocity regulator may be configured to control the speed of movement of the actuation mechanism until the needle insertion step of the actuation process has been completed. Whilst the illustrated example includes two opposing counter-surfaces the skilled person will appreciate that more or less features may be utilised in embodiments of the invention.

In the illustrated device the cam surface defines a substantially constant helical cam path but the skilled person will appreciate that the surface may have other sloped profiles (for example, a variable angle of incline) depending upon the velocity profile required for the forward movement of the plunger 110. Whilst an arrangement having two compression springs is advantageous in providing a compact actuation mechanism the skilled person will appreciate that in some embodiments only a single compression may be utilised. For example, in a single spring arrangement, the cam members could be formed on a portion of the plunger and the plunger may be allowed to rotate relative to the housing.

Exemplary autoinjector devices are disclosed herein that may incorporate one or more of the features of the autoinjector 1 discussed above and also incorporating one or more features discussed below.

Exemplary injection (e.g. autoinjector) devices may comprise a mechanism for releasing an interlock to initiate the device for activation by a user. The interlock may be configured to retain an insertion driver, which may be a drive spring such as the first drive spring 120 discussed above. Upon actuation of the interlock, the insertion driver is no longer retained and is free to act to insert the needle 6 into an injection site, optionally on additional actuation of the trigger button 40.

In known injection devices, the interlock may be actuated by an interlock actuator, such as a lock out shroud. The lock out shroud may protrude from a forward end of the device and be configured to move rearward within the injection device on depression thereof, for example by a user pressing the lock out shroud against the skin surrounding an injection site. The lock out shroud moves rearward into a clearance volume within the injection device and is coupled either directly or indirectly to the interlock to actuate it and release the insertion driver. It is noted that in all devices disclosed herein, further action, such as depression of the trigger button, may be required to "fire" the device and operate the insertion driver.

In exemplary injection devices, the interlock actuator, which may be a lock out shroud, is moveable from a stowed position and an operable position. Movement of the interlock actuator from the stowed position to the operable position couples the interlock actuator to the interlock such that, after movement of the interlock actuator from the stowed position to the operable position, movement of the interlock actuator back towards the stowed position actuates the interlock and releases the insertion driver ready to be fired.

In exemplary arrangements, the interlock actuator may be pulled out of the injection device to move it from the stowed position to the operable position. Alternatively or in addition, the interlock actuator may be moved from the stowed position to the operable position under a force exerted by a spring or other biasing/driving means. That is, in the stowed position the interlock actuator may be inserted further into the injection device than in the operable position such that the dimensions of the injection device are reduced. This reduces the overall size of the injection device when not in use.

As mentioned above, the interlock actuator must have a clearance volume within the injection device into which it can travel in order to actuate the interlock. In exemplary arrangements, the interlock actuator may occupy the clearance volume when in the stowed position. For example, in the stowed position, the interlock actuator may be positioned at least partly within the injection device such that it abuts a mechanical limit or end stop.

Movement of the interlock actuator to the operable position pulls it away from the mechanical limit and provides a clearance volume between the interlock actuator and the mechanical limit into which the interlock actuator may travel to actuate the interlock. Movement of the interlock actuator from the stowed position to the operable position also couples the interlock actuator to the interlock such that movement of the interlock actuator into the now available clearance volume actuates the interlock.

Figure 7:
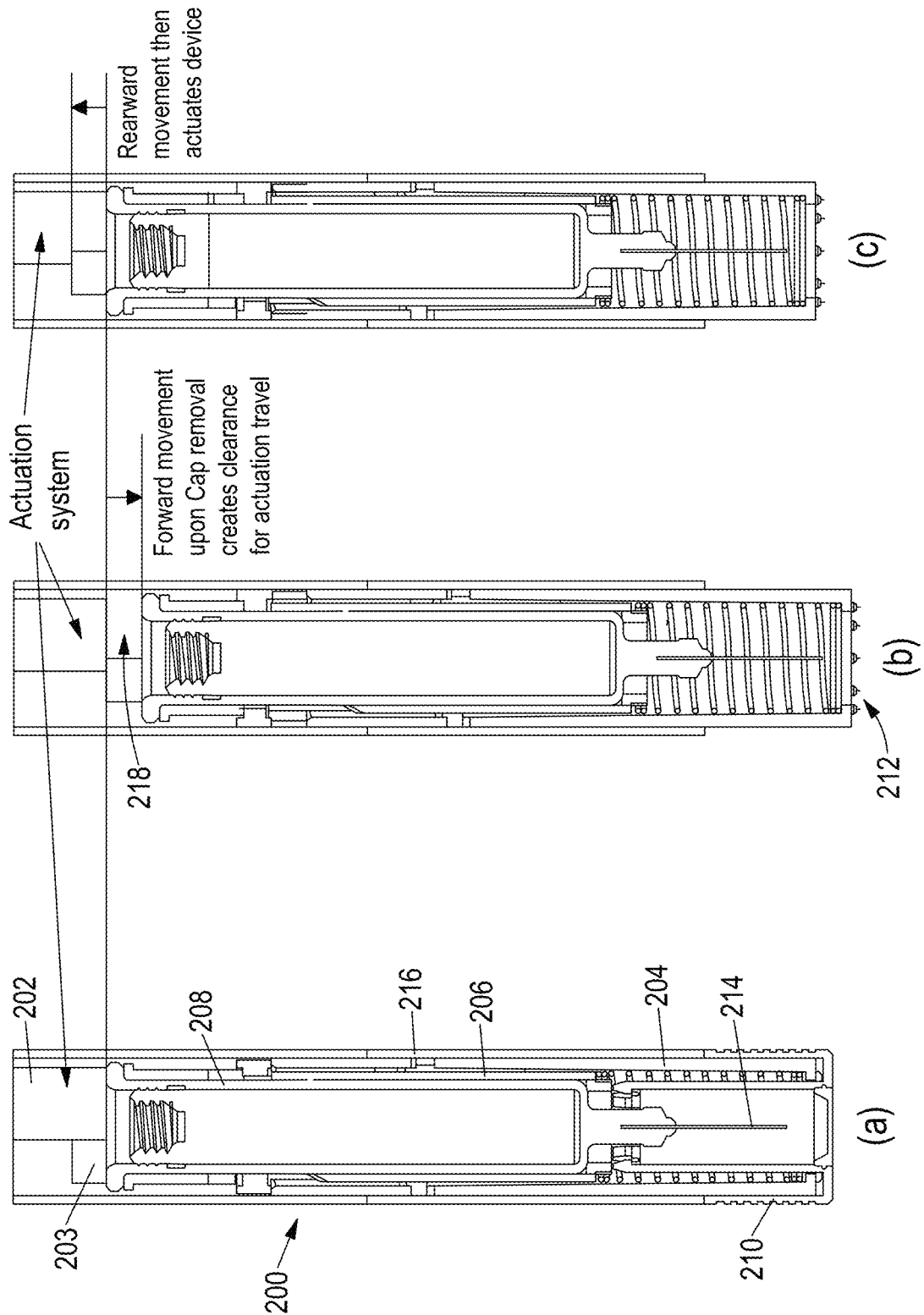
FIGS. 7a-c show an injection device at various stages of operation.

This is shown conceptually in FIGS. 7a-c, which show part of an injection device 200. In FIGS. 7a-c, the interlock is not shown and is located above the blocks 202 and 203, which conceptually show an actuation system that is coupled to the interlock and configured to actuate it. In the exemplary arrangement of FIGS. 7a-c, an interlock actuator comprises a lock out shroud 204, a syringe carrier 206 and a syringe barrel 208.

It is noted that in other arrangements, the interlock actuator might not include the syringe carrier 206 and/or the syringe barrel 208. In such arrangements, the interlock actuator may be configured to translate linear axial motion to the actuation system without moving the syringe barrel 208. For example, one or more members of the interlock actuator may be configured to travel adjacent to the syringe to translate linear axial motion thereof to the actuation system 202, 203 sitting rearward of the syringe.

In exemplary arrangements, the interlock actuator is configured to translate axial linear motion at the lock out shroud 204 to the actuation system 202.

In FIG. 7a, the interlock actuator is against a mechanical limit (or end stop) such that it cannot travel any further rearward. A cap 210 is fitted to the forward end of the injection device 200. The cap 210 is removable to expose an opening 212 in the forward end of the injection device 200. A needle 214 of the syringe is located within the opening 212.

As can be seen in FIG. 7b, removal of the cap 210 also moves the interlock actuator from the stowed position to an operable position, in which the components of the interlock actuator are shifted axially in the injection device 200. In the exemplary arrangement of FIG. 7b, the interlock actuator is shifted forward in the injection device 200 such that the lock out shroud 204 extends further from a body 216 of the injection device 200 than when the interlock actuator is in the stowed position. Axial forward movement of the interlock actuator moves the interlock actuator away from the mechanical limit and creates clearance 218 within the injection device 200 into which the interlock actuator can move during operation thereof.

In addition, removal of the cap 210 couples the interlock actuator to the interlock. In FIG. 7b, this is achieved by movement of the block 203 into the clearance gap 218, which may be done under a biasing force.

As shown in FIG. 7c, the lock out shroud 204 may now be moved rearward until it meets the mechanical limit. This may be achieved by a user pressing the lock out shroud 204 against an intended injection site, such as a patient's skin. Rearward movement of the interlock actuator pushes the actuation system 202, 203 rearward to actuate the interlock and release the insertion driver (not shown in FIGS. 7a-c), which will drive the syringe 208 forwards to insert the needle into the injection site.

FIGS. 8a-e show a rear section 300 of an injection device in various stages of operation. The rear section 300 accommodates an actuation system comprising an insertion tube 302, a rear body 304, an actuation collar 306 and an insertion driver 308, which in this case is a compression spring although other types of spring or driving means could be used. Each of these features is shown individually in FIGS. 9a-d.

The insertion tube 302 comprises a tubular body 310 and a pair of radially extending pips 312 (only one pip is visible in FIG. 9a) on opposite sides of a sidewall of the insertion tube 302. Each pip 312 is configured to run through corresponding actuation tracks 314 of the actuation collar 306. Each pip is a generally teardrop shape with the point 316 of the teardrop facing rearward. The teardrop shape is also skewed in one direction in order to guarantee a particular direction of travel of the pips 312 through the actuation tracks 314. In the exemplary insertion tube 302 of FIG. 9a, the pip is partially rotated anticlockwise. It is noted that other shaped pips may also be used, for example the pip may have a generally rectangular shape with a chamfered corner configured to guide the pip along the correct section of the actuation track. In a specific example, a rectangular pip may be elongate in a longitudinal direction of the injection device and one of the rear corners may be chamfered.

The insertion tube 302 also comprises insertion tracks 318 running substantially longitudinally along opposite sides of the outer wall of the insertion tube 302. The insertion tracks 318 include dogleg sections approximately a quarter of the way forwards along the length of the tracks 318 from the rear of the track 318.

The rear body 304 has a broadly tubular shape having a number of features and tracks thereon. In particular, the rear body 304 comprises driver tracks 320 on opposite sides of a sidewall of the rear body 304 and configured to support lugs 322 of an insertion collar 324 fixed to one end of the insertion spring 308. The driver tracks 320 have a V-shape and also each include a vertical slot 326 extending forwards from an end of one arm of the "V".

When the rear section 300 is constructed, the insertion tube 302 is rotatably and slidably fitted within the rear body 304. The insertion spring 308 is positioned within the insertion tube such that the lugs 322 extend through the insertion tracks 318 and rest on the driver tracks 320. The actuation collar 306 is positioned at a rearward end of the rear body 304 and the pips 312 extend through the actuation tracks 314. The actuation collar 306 is fixed in relation to the rear body 304.

Referring to FIGS. 8a-e, motion of the features of one side of the rear section 300 is described but it is noted that similar function is provided on the opposite side of the rear section 300. In FIG. 8a, the pip 312 is positioned at an extreme end of the actuation track 314, which forms a valley deep enough to receive the pip 312. The valley is configured to retain the pip 312 to prevent the insertion spring 308 from driving the insertion tube 302 forwards in the injection device. The lug 322 on the insertion collar 324 is biased forwards because the insertion spring 308 is compressed against a rearward surface of the device. The lug 322 is therefore urged to descend a declined (or forwardly extending) extension ramp 330 of the driver track 320. Because the lug 322 is retained within the insertion track 318, motion of the lug 322 down the extension ramp 330 would rotate the insertion tube 302 and this is prevented by retention of the pip 312 in the valley of the actuation track. The force applied by the insertion spring 308 on the lugs 322 also holds the pip 312 in the valley by a similar process.

The rear section 300 also comprises a volume 332 into which a barrel of a syringe may be fitted and connections 324 configured to connect a front section of the injection device thereto, for example by snap fit.

In FIG. 8b, a syringe barrel 336 has been inserted into the volume 332 and a front section 338 of the injection device fitted to the connections 334. The volume 332 is too short to receive the syringe barrel 336 completely and so a flange 340 of the syringe barrel 336 pushes the insertion tube 302 rearwards. The pip 312 is therefore moved rearwards out of the valley along a first inclined section 342 of the actuation track 314 which imparts a rotational force on the insertion tube 302. The rotation is clockwise when looking forwards along the injection device and this frame of reference is used in the following to aid description of the operation of the device.

The clockwise rotation of the insertion tube 302 caused by movement of the pip 312 in the actuation track 314 allows the lug 322 of the insertion collar 324 to move part way down the declined extension ramp 330 of the driver track 320 towards the bottom of the "V". In other arrangements, the driver track may include an inclined section corresponding to the first inclined section 342 of the actuation track 314.

In this position, the interlock actuator is in a stowed position. The interlock actuator is at its most rearward position and has reached a mechanical limit because the pip 312 cannot move any further in the actuation track 314. Because of this rearward travel of the interlock actuator, the injection device is smaller than when it is ready for use because no clearance volume exists within the device for the interlock actuator to travel into to actuate the interlock. The interlock actuator and/or any associated components such as the actuation system occupy the clearance volume.

The interlock actuator is prevented from forward motion by a stowage lock, for example by the cap at the forward end of the injection device as shown in FIGS. 7a-c. The insertion spring 308 provides a biasing force urging the lug 322 and therefore the insertion tube 302 forwards.

The interlock actuator in the exemplary injection device of FIGS. 8a-e acts through the syringe barrel 336 in a similar way to that shown in FIGS. 7a-c. In a specific arrangement, the interlock actuator includes the lock out shroud, the syringe barrel 336 and the syringe carrier 344, as explained above in respect of FIGS. 7a-c. The lock out shroud, syringe carrier 344 and syringe barrel 336 are linearly coupled such that linear axial movement of one is translated to linear axial movement of the others. However, as discussed above, this need not be the case and the skilled person will appreciate that the interlock actuator could act around the side of the syringe barrel 336 to act upon the actuation system.

In FIG. 8c, the cap has been removed from the injection device and the interlock actuator has therefore moved from the stowed position to an operable position. In the exemplary arrangement of FIGS. 8a-e, movement of the interlock actuator to the operable position is provided by the force exerted by the insertion spring 308 once the cap is removed.

The lug 322 is urged down the declined extension ramp 330 of the driver track 320 until it rests at the bottom of the "V". Movement of the lug 322 down the extension ramp 330 imparts a clockwise rotation on the insertion tube 302. The pip 312 therefore travels down a declined section 346 of the actuation track 314, which moves the insertion tube 302 and the interlock actuator forwards. In the exemplary arrangement of FIGS. 8a-e, this results in the lock out shroud extending from the forward end of the device.

The interlock is now preventing the syringe from moving further forwards such that the needle extends from the forward end of the injection device. The interlock in the exemplary arrangement of FIG. 8c is provided by the lug 322 sitting at the bottom of the "V" formed in the driver track 320 and unable to move up a rearwardly extending (or inclined) interlock ramp 350 because of the force exerted by the insertion spring 308 on the lug 322. This, along with the pip 312 sitting at the bottom of a "V" formed by the declined section 346 and a second inclined section (an interlock section) 348 of the actuation track 314, prevents further clockwise rotation to release the insertion spring 308 fully. The interlock section 348 of the actuation track 314 corresponds to the interlock ramp 350 of the driver track 320 in that the pip 312 moves in the interlock section 348 while the lug 322 moves on the interlock ramp 350.

As can be seen in FIG. 8c, a clearance volume 352 now exists between the rearward end of the insertion tube 302 and the rearward surface of the injection device against which the insertion spring 308 acts. The interlock actuator may now move rearward within the injection device making use of that clearance volume 352. Because of the altered geometry of the actuation system (i.e. the altered positions of the pip 312 and the lug 322), the interlock actuator is now coupled to the actuation system and the interlock. Coupling in this sense means that movement of the interlock actuator rearwards will result in movement of the actuation system. Movement of the interlock actuator back towards the stowed position now actuates the interlock and releases the insertion spring 308. In the exemplary arrangement of FIGS. 8a-e, forward axial linear movement of the interlock actuator moves it from the stowed position to the operable position. Accordingly, rearward linear axial movement of the interlock actuator after movement to the operable position actuates the interlock.

Referring to FIG. 8d, the lock out shroud is pressed against an injection site and is pushed rearwards. This moves the other features of the interlock actuator rearwards and engages the actuation system. The insertion tube 302 moves rearwards into the clearance volume 352. Because the pip 312 is skewed (i.e. rotated anti-clockwise) the point 316 of the pip 312 is directed towards the second inclined section 348 of the actuation track 314. This will guide the pip 312 into the second inclined section 348 of the actuation track 314 as the insertion tube 302 moves rearwards. The pip 312 therefore travels in the second inclined section 348 of the actuation track 314, which rotates the insertion tube 302 clockwise. Because the lug 322 is retained in the insertion track 318, it is moved up an interlock ramp 350 along the driver track 320 towards the vertical slot 326.

In FIG. 8d, the lug 322 is aligned with the vertical slot 326 and is therefore free to move forwards under the force of the insertion spring 308. Further, the pip 312 is aligned with a vertical section 354 of the actuation track 314. In this position, the interlock has been actuated and the needle may be inserted into the injection site.

In FIG. 8e, the lug has moved down the vertical slot 326 in the rear body 304 under the force exerted by the insertion spring 308. This moves the pip 312 down the vertical section of the actuation track 314 because the lug 322 is in contact with an angled face in the insertion slot 318 caused by the dogleg. The insertion tube 302 is prevented from rotating clockwise because of the vertical section 354 of the actuation track 314 until the pip 312 reaches a locking recess 356 at the end of the vertical section 354. At this point, the lug 322 acts on the angled surface of the dogleg in the insertion track 318 and rotates the pip 312 into the locking recess 356. The lug is now aligned with the forward portion of the insertion recess 318 that is forward of the dogleg and so the insertion spring 308 can extend fully and insert the needle into the injection site.

The declined section 330 of the driver track 320 corresponds to the declined section 346 of the actuation track 314 in that the lug 322 moves along the declined section 330 of the driver track 320 when the pip 312 moves along the declined section 346 of the actuation track 314. Further, the interlock ramp 350 of the driver track 320 corresponds to the second inclined section 348 of the actuation track 314 in that the lug 322 moves along the interlock ramp 350 of the driver track 320 when the pip 312 moves along the second inclined section 348 of the actuation track 314.

However, the steepness of the inclines and declines of the driver track is less than the steepness of the inclines and declines of the actuation track. That is, the angle of the declined section 330 of the driver track 320 is less than the angle of the declined section 346 of the actuation track 314, and the angle of the interlock ramp 350 of the driver track 320 is less than the angle of the second inclined section 348 of the actuation track 314.

This arrangement means that a geared or ratioed relationship exists between linear axial movement of the lug 322 and linear axial movement of the pip 312. Therefore, the biasing force exerted by the insertion spring 308 on the lug is overcome with less force, but greater linear motion, of the interlock actuator.

In other exemplary arrangements, there is no need for separate actuation tracks and driver tracks and only one of the pip or the lug need be used.

FIGS. 10a-e show an exemplary rear section 400 of an injection device in various stages of operation. The rear section 400 accommodates an actuation system comprising an insertion tube 402, a rear body 404, an actuation collar 406 and an insertion driver 408, which in this case is a compression spring although other types of spring or driving means could be used. Each of these features is shown individually in FIGS. 11a-d.

Some of the features of the exemplary rear section 400 are the same or similar to the corresponding features of the rear section 300 described above. These features are not therefore discussed again in detail.

The insertion tube 402 comprises a tubular body and a pair of radially extending pips 412 (only one pip is visible in FIG. 11a) on opposite sides of a sidewall of the insertion tube 402. Each pip 412 is configured to run along corresponding actuation tracks 414 of the actuation collar 406. Each pip 412 is a generally rectangular shaped with a chamfered corner configured to guide the pip 412 along the correct section of the actuation track 414. In the specific example of FIGS. 10 and 11, a rectangular pip 412 is elongate in a longitudinal direction of the injection device and one of the rear corners is chamfered.

The actuation collar 406 forms part of a trigger button 407 for triggering the device and delivering the dose of medicament. The actuation track 414 is formed on a forward edge of the trigger button 407 and comprises a plurality of ramped surfaces arranged to operate the device as set out below. In particular, the actuation track comprises a first inclined section 442 against which the pip 412 travels rearward, a declined section 446 against which the pip 412 travels forward, and a second inclined section (or interlock section) 448. A corresponding actuation track is formed on an opposite side of the actuation collar 406.

Figure 8:
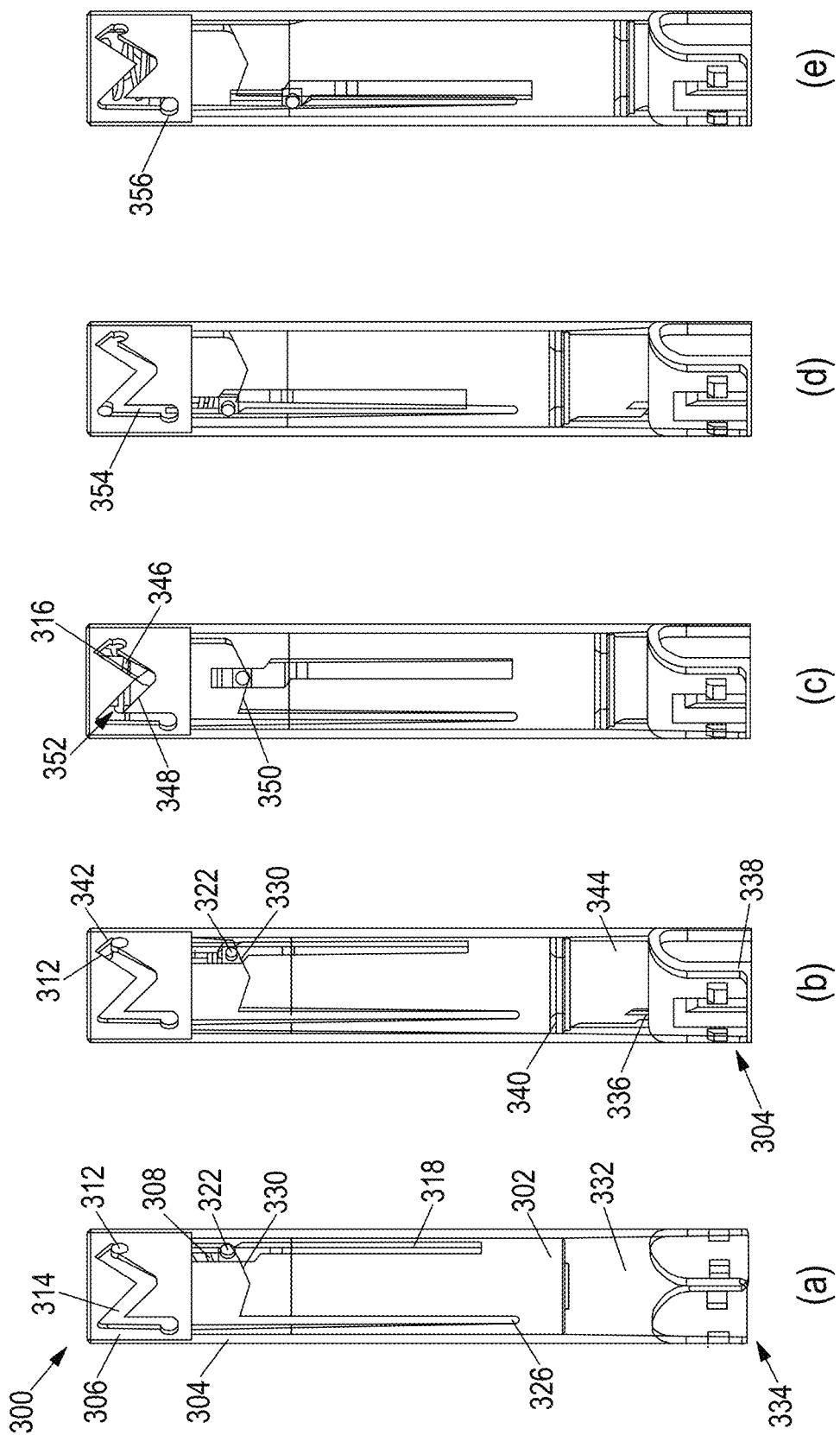
FIGS. 8a-e show an injection device at various stages of operation.
Figure 9:
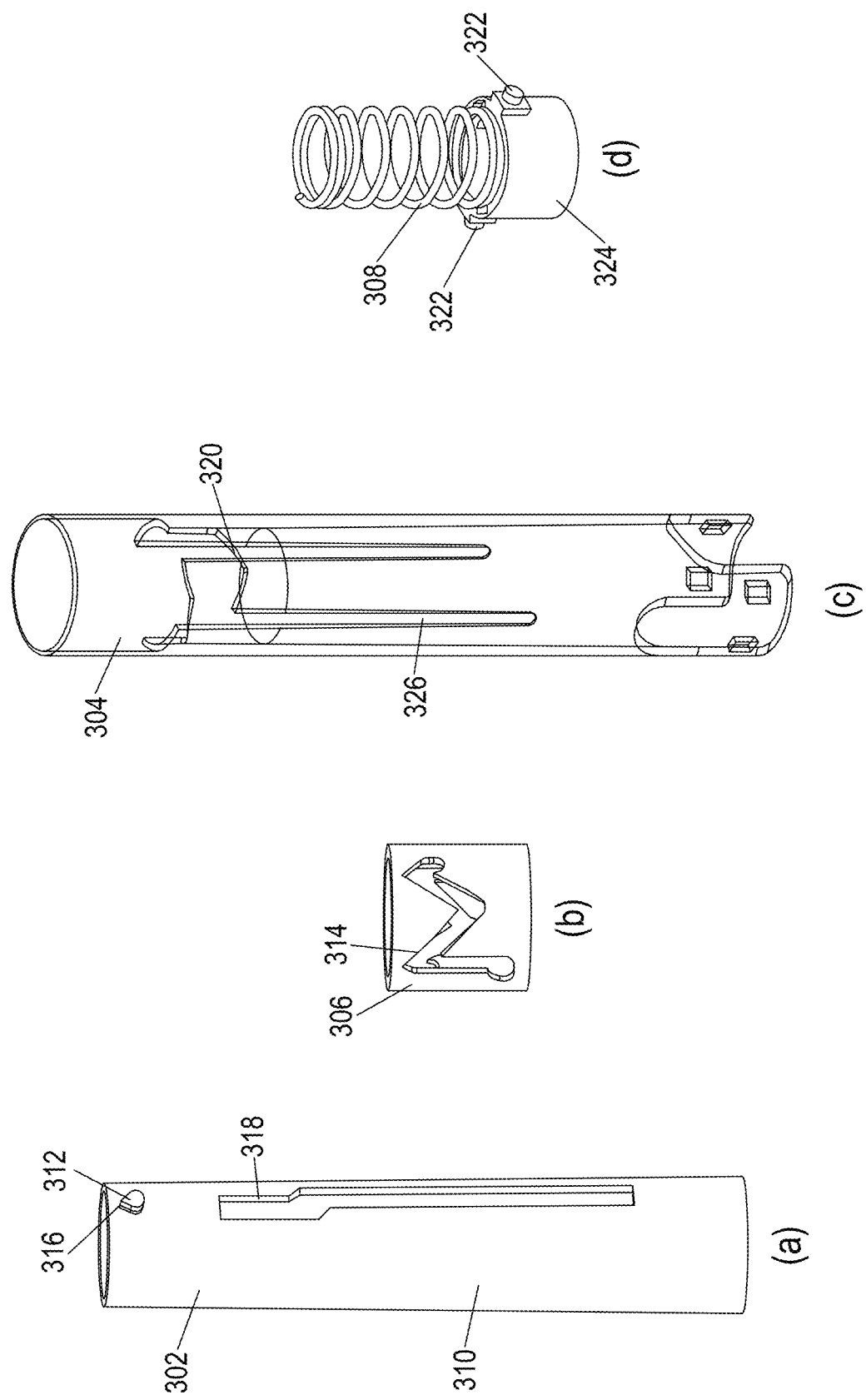
FIGS. 9a-d show features of the injection device of FIGS. 8a-e.
Figure 10:
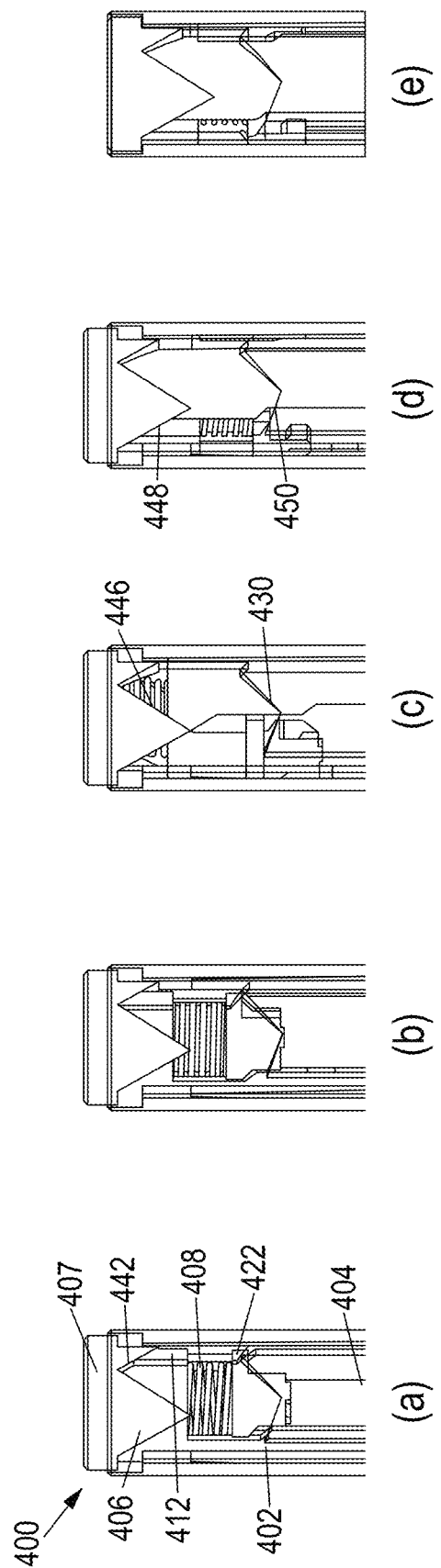
FIGS. 10a-e show an injection device at various stages of operation.
Figure 11:
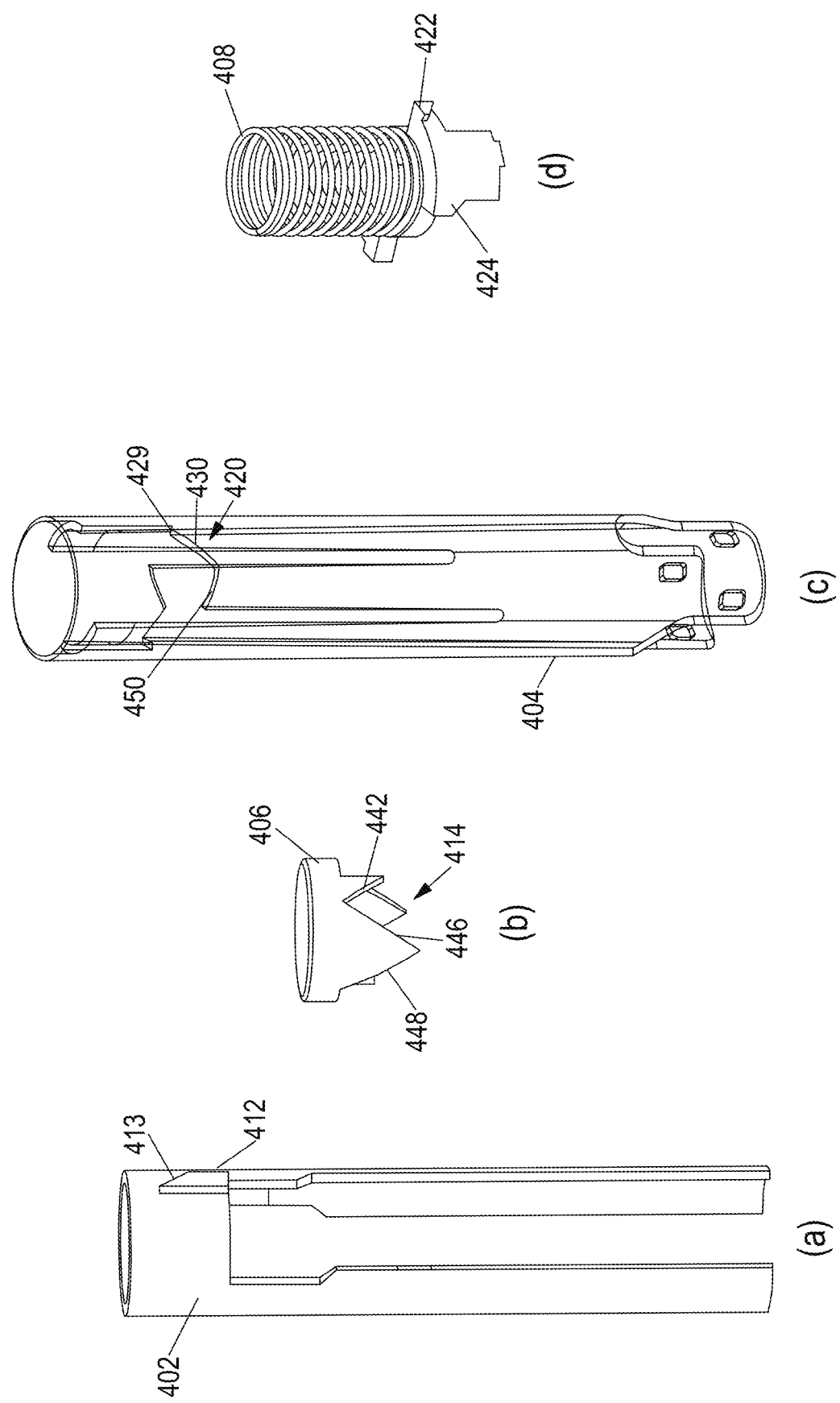
FIGS. 11a-d show features of the injection device of FIGS. 10a-e.

As with the rear body of FIGS. 8 and 9, the rear body 404 comprises a driver track 420 including an extension ramp 430 and an interlock ramp 450. The driver track 420 also includes a locking ramp 429 along which a collar lug 422 travels rearwards to meet the extension ramp 430.

When the rear section 400 is constructed, the insertion tube 402 is rotatably and slidably fitted within the rear body 404. The insertion spring 408 is positioned within the insertion tube 402 such that the lugs 422 extend through insertion tracks in the insertion tube 402 and rest on the driver tracks 420. The actuation collar 406 is positioned at a rearward end of the rear body 404 and the pips 412 extend radially to interact with the actuation tracks 414. The actuation collar 406 is rotationally fixed in relation to the rear body 404.

Referring to FIGS. 10a-e, operation of the rear section 300 is described below.

In FIG. 10a, the insertion tube 402 sits slightly forward of its most rearward position. The force exerted by the insertion driver 408 pushes the collar lug 422 on the collar 424 down the locking ramp 429 of the driver track 420. The collar lug 422 is held in a vertical slot in the insertion tube 402 and a rotational force is therefore imparted to the insertion tube 402. This force urges the pip 412 against the first inclined section 442 in the actuation track 414, holding it in place for transit.

In FIG. 10b, a syringe has been inserted into the device and the insertion tube 402 is pushed rearward by the syringe flange. The pip 412 travels along the first inclined section 442 and the collar lug 422 is displaced rearwards to the top of the locking ramp 429. A rotational force is generated by the insertion spring 408 acting on the collar lug 422 and the extension ramp 430. The rotational force urges the pip 412 forwards along the declined section 446 of the actuation track 414. Travel of the pip 412 along the declined section is resisted by the presence of the syringe flange, which is prevented from moving forwards, for example by a cap.

As shown in FIG. 10c, when the cap (or other means for preventing movement of the syringe) is removed, the syringe (which may be in a syringe carrier) is free to move forwards. The insertion tube 402 pushes the syringe forwards under the force of the insertion spring 408. The pip 412 travels along the declined section 442 which imparts a rotational force on the collar lug 422 to move it to a forward end of the extension ramp 430. The pip 412 travels to a point whereby rearward movement of the pip 412 ensures travel along the second inclined section 448 due to the chamfered corner of the pip 412. The fact that the pip 412 will travel along the second inclined section 448 to actuate the interlock means that the interlock actuator is now coupled to the actuation system. The device is now held by the interlock.

As shown in FIG. 10d, the interlock actuator, for example comprising a lock out shroud, pushes the syringe rearward and this in turn pushes the insertion tube 402 rearward. T pip 412 therefore travels rearward along the second inclined section 448 of the actuation track 414. This forces the collar lug 422 rearwards along the interlock ramp 450 of the driver track 420 until it reaches a point close to a rearward end of the interlock ramp 450.

As shown in FIG. 10e, pressing the button 407 displaces the button 407 and the actuation track 414 forwards and brings the insertion tube pip 412 to the end of the second inclined section 448. This causes the collar lug 422 to pass the rearward end of the interlock ramp 450 and the insertion spring 408 acts on the insertion tube 402 to drive it and the syringe forwards to insert the needle into the injection site. This activates the device.

The skilled person will appreciate that other exemplary arrangements are possible within the scope of the appended claims.

The invention claimed is:

1. An injection device for receiving a syringe therein and for delivering a dose of medicament from the syringe, the injection device comprising:
    an insertion driver comprising a drive spring configured to drive the syringe forwards within the injection device for inserting a needle of the syringe into an injection site;
    an interlock configured to retain the insertion driver in a primed state and, when actuated, to allow the insertion driver to drive the syringe forwards; and
    an interlock actuator moveable between a stowed position and an operable position,
        wherein in the stowed position the interlock actuator is positioned further into the injection device than in the operable position,
        wherein movement of the interlock actuator from the stowed position to the operable position provides a clearance volume into which the interlock actuator can travel in order to actuate the interlock, and
        wherein movement from the stowed position to the operable position couples the interlock actuator to an actuation system such that movement from the operable position back towards the stowed position and into the clearance volume actuates the interlock.

2. An injection device according to claim 1, wherein the interlock actuator comprises a lock out shroud at least partially received within the injection device.

3. An injection device according to claim 2, wherein the lock out shroud is configured to move forward from the stowed position such that it extends from a forward end of the injection device in the operable position.

4. An injection device according to claim 2, wherein the interlock actuator further comprises one or more of at least part of a syringe carrier and at least part of a barrel of the syringe.

5. An injection device according to claim 1, wherein the interlock comprises a rearwardly extending interlock ramp and a lug linearly coupled to the syringe and forward biased onto the interlock ramp to resist travel of the lug rearwards on the interlock ramp.

6. An injection device according to claim 5, wherein the lug is linearly coupled to the interlock actuator such that movement of the interlock actuator from the operable position towards the stowed position causes the lug to travel rearwards on the interlock ramp.

7. An injection device according to claim 6, wherein the interlock further comprises a vertical slot extending from a rearward end of the interlock ramp, and wherein the interlock actuator is moveable from the stowed position towards the operable position to align the lug with the vertical slot.

8. An injection device according to claim 7, wherein the insertion driver is configured to drive the lug forwards into the vertical slot and thereby to drive the syringe forwards to insert the needle into the injection site.

9. An injection device according to claim 1, wherein the insertion driver is further configured to bias the interlock actuator from the stowed position towards the operable position, the injection device further comprising a stowage lock configured to retain the interlock actuator in the stowed position until release thereof.

10. An injection device according to claim 9, wherein the stowage lock comprises a cap removably fitted to the injection device, and wherein removal of the cap releases the stowage lock.

11. An injection device according to claim 9 when dependent on claim 5, further comprising a forwardly extending extension ramp, the forward end of the extension ramp meeting the forward end of the interlock ramp to form a V-shape, wherein the lug is linearly coupled to the interlock actuator and wherein release of the stowage lock allows the insertion driver to cause the lug to travel down the extension ramp such that the lug is at the bottom of the V-shape and the interlock actuator is in the operable position.

12. An injection device according to claim 11, wherein the actuation system comprises a guide system configured, on movement of the interlock actuator from the operable position towards the stowed position, to ensure the lug travels along the interlock ramp and not along the extension ramp.

13. An injection device according to claim 12, wherein the guide system comprises a track operable with the lug to guide the lug to ensure it travels along the interlock ramp and not along the extension ramp.

14. An injection device according to claim 1, wherein a biasing means resists actuation of the interlock, and wherein the actuation system is configured to provide geared movement of the interlock actuator and the interlock against the biasing means.

15. An injection device according to claim 14, wherein the interlock comprises a rearwardly extending interlock ramp and a lug linearly coupled to the syringe and forward biased onto the interlock ramp to resist travel of the lug rearwards on the interlock ramp, and wherein the actuation system comprises an actuation track and a pip configured to move within the actuation track, wherein the pip is rotationally coupled to the lug such that it moves within an interlock section of the actuation track when the lug moves on the interlock ramp, and wherein the interlock section of the actuation track has a steeper rearward incline than the interlock ramp.

16. An injection device according to claim 15, wherein the actuation system comprises a guide system configured, on movement of the interlock actuator from the operable position towards the stowed position, to ensure the lug travels along the interlock ramp and not along the extension ramp, and wherein the guide system comprises the pip and the actuation track, and wherein the pip and the actuation track are configured to cooperate to guide the pip into the interlock section.

17. An injection device according to claim 16, wherein the pip has a tear drop shape with the tip facing substantially rearward.

18. An injection device according to claim 17, wherein the pip is skewed such that the tip is biased in one direction away from a longitudinal axis of the for guiding the pip into the interlock section.

19. An injection device according to claim 1, wherein a length of the injection device is less when the interlock actuator is in the stowed position than when the interlock actuator is in the operable position.

20. A rear section of an injection device for attachment to a front section to form the injection device, wherein the injection device is for receiving a syringe therein and for delivering a dose of medicament from the syringe, the rear section comprising:

an insertion driver comprising a drive spring configured to drive the syringe forwards within the injection device for inserting a needle of the syringe into an injection site;

an interlock configured to retain the insertion driver in a primed state and, when actuated, to allow the insertion driver to drive the syringe forwards; and an actuation system which couples to an interlock actuator when the interlock actuator is moved from a stowed position to an operable position, wherein in the stowed position the interlock actuator is positioned further into the injection device than in the operable position, wherein movement of the interlock actuator from the stowed position to the operable position provides a clearance volume into which the interlock actuator can travel in order to actuate the interlock, and wherein, as a result of the coupling the interlock actuator to the actuation system, movement of the interlock actuator from the operable position back towards the stowed position and into the clearance volume actuates the interlock.

\* \* \* \* \*